United States Patent [19]

Martinez Martinez et al.

[11] 4,136,679
[45] Jan. 30, 1979

[54] PROCESS FOR THE ROTATION OF FETAL HEAD DURING CHILDBIRTH

[76] Inventors: Eduardo G. Martínez Martínez, 458, St. Domingo St. Guanabacoa; Guillermo Azcarraga Maig, 657, 26 St. Nuevo Vedado; Emilio Soto Méndez, 555, Tres Palacios St. Luyano; Eduardo Rodríguez Calderón, 262, Agucate St.; Nicanor Menéndez Mesa, 9523, Vento Ave. Alta Habana, all of Havana, Cuba

[21] Appl. No.: 673,102

[22] Filed: Apr. 2, 1976

[30] Foreign Application Priority Data

Apr. 11, 1975 [CU] Cuba .................................. 34249

[51] Int. Cl.² .................................................. A61B 17/42
[52] U.S. Cl. .................................... 128/1 R; 128/352; 128/361
[58] Field of Search .................... 128/303 R, 361; 128/352, 20, 1 R

[56] References Cited

U.S. PATENT DOCUMENTS

3,776,240  12/1973  Woodson ........................... 128/361

FOREIGN PATENT DOCUMENTS

993416  7/1951  France .................................. 128/361
1228043  3/1960  France .................................. 128/361

OTHER PUBLICATIONS

Weisman, "Experiences with the Murless Head Extractor in Cesarean Section", in J.A.M.A., 150[12]: 1209–1212, 1952.

Primary Examiner—Robert W. Michell
Assistant Examiner—Michael H. Thaler
Attorney, Agent, or Firm—Haseltine, Lake & Waters

[57] ABSTRACT

Process for rotation of the fetal head during childbirth, using a force through the agency of spatulas by applying the principle of wheel rotation, namely for rotating the head in any of its presentations of position, to reduce fetal and maternal lesions, as well as the necessity of cesarean sections, and to facilitate manipulation by less skilled personnel; the process comprising rotating the head by applying the force at a point corresponding to the zone of the occipital bone, utilizing the axis of rotation which passes through the junction of the cervical column with the fetal occiput, and using the spatulas of specific shapes. An instrument is also disclosed for the rotation of the fetal head, comprising a pistol-grip handle, and a pedical terminating in a solid scoop, the latter presenting a pelvic curvature and a cephalic curvature, the axis of the tip of the scoop having a specific angular inclination relative to the longitudinal axis of the instrument.

4 Claims, 8 Drawing Figures

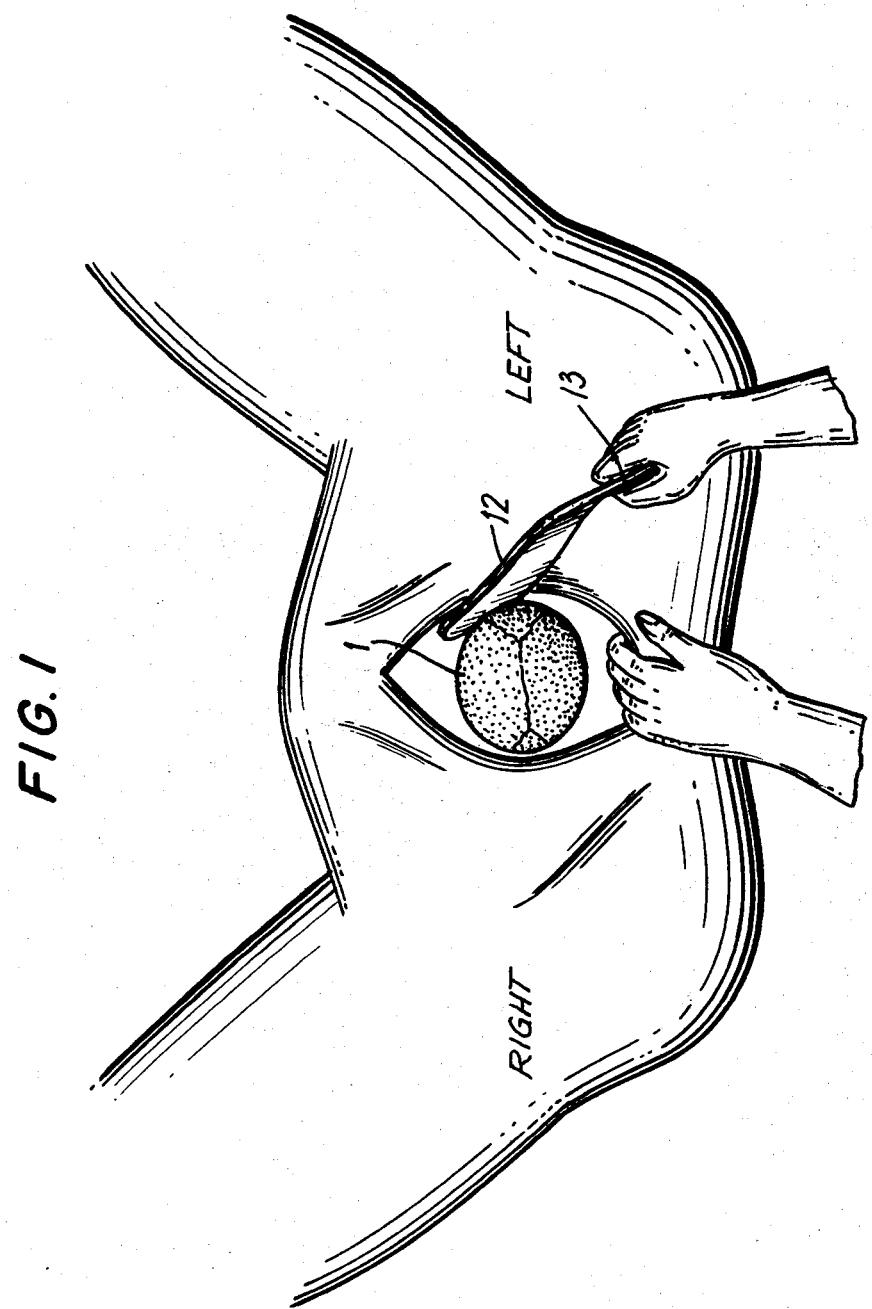

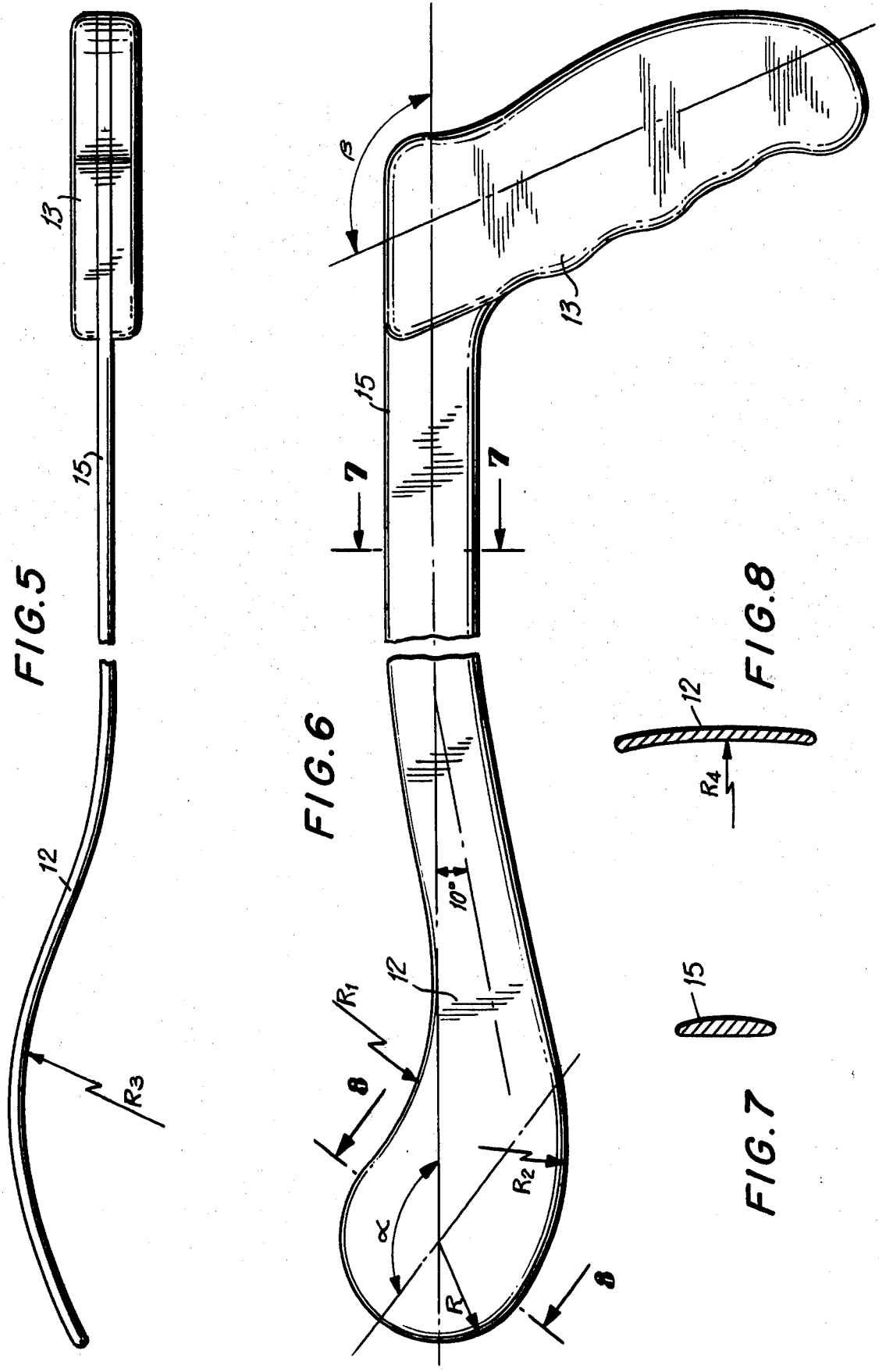

PROCESS FOR THE ROTATION OF FETAL HEAD DURING CHILDBIRTH

FIELD OF THE INVENTION

This invention concerns the field of medicine, in the branch of obstetrics and gynecology.

Prior Art

Instruments and methods are known for obtaining rotation of the head a fetus during delivery.

The forceps invented by Chamberlen in the seventeenth century, as stated in all the standard works on obstetrics, is based on the tongs principle and serves to rotate and extract the fetal head in the delivery. It should be understood that in the following, the expression "fetal head" and "head" will be used interchangeably, even though during childbirth one might actually mention the "head of the newborn baby". The known forceps is composed of two crossed blades united by a joint. Each blade consists of a fenestrated or solid scoop, a pedicle had a handgrip. It works by compressing compression of the head of the fetus. These scoops are not easy to manipulate and entail considerable risk for the mother and the fetus.

Also known is the spatula, such as in Japanese Pat. 46-11316 and those invented by Thierry in France in 1950. Based on the principle of the lever of the first orders, this serves to rotate and extract the head of fetus during delivery. This instrument consists of two blades not jointed together but acting independently. Each blade consists of a solid scoop, a pedicle and a horizontal handgrip. It works by leverage and does not compress the head of the fetus. However, it is not easy to handle, although the risk for mother and fetus is less than with the forceps. The disadvantages of the methods and instruments described reside in their complex handling, which gives rise to considerable risks to mother and fetus.

SUMMARY OF THE INVENTION

The procedure proposed is founded on the principle of rotation of bodies and consists in making the head of the fetus turn about an axis of rotation which is at the junction of the cervical column with the occipital bone of the fetus, it being possible to vary the axis of rotation according to the degree of flexion of the head of the fetus.

The proposed instrument is of special shape for adaptation to the procedure. The scoop has a pelvic curvature and a further cephalic curvature, the radii of which are much less than those of the scoops of existing instruments. The tip or nib of the scoop defines an angle with the axis of the instrument similar to the angle formed by the axis of the handgrip with the axis of the instrument. The class of the curvatures causes the application of the instrument in the direct anterior variety to be occipitoparietal and not parietomolar as is the case with other types of instrument. Also, the curvatures have the object of applying a force in a definite region of the head of the fetus.

In the inventive method, one blade is inserted on the side corresponding to the fetal occiput, the remaining blade being placed in the material pelvis as though in a direct approach. At the instant when a uterine contraction takes place, the scoop is applied in such a way that the greater share of the forces may be applied above the axis of rotation by means of a moderate rotory movement of the handgrip.

BRIEF DESCRIPTION OF THE DRAWINGS

The inventive process and instrument will now be described in full detail wth reference to the accompanying drawings, wherein FIG. 1 is a somewhat schematic illustration of using the inventive instrument in a first manner of practicing the process;

FIGS. 5 and 6 are respective plan and front elevational views of an examplary (left-hand) instrument blades according to the invention; and FIGS. 7 and 8 are respective sectional views taken in FIG. 6 along the lines 7—7 and 8—8.

Before explaining the inventive method, the instrument should first be described as shown in FIGS. 5 through 8. The instrument may be left- or right-handed, as customary in obstetrics, only one being illustrated while the other will of course be a reversal of what is being shown.

The instrument includes a scoop 12 across which a section is taken in FIG. 8, showing a slight curvature therein, independent of the curvature that can be seen in FIG. 5 toward the left-hand end of the instrument. A handgrip 13 carries the scoop by the intermediary of a pedicle 15, as shown. Further details will become better understood as the description proceeds.

DETAILED DESCRIPTION

The inventive method for rotating the fetal head during childbirth is founded on the principle of the rotation of wheels, the blade of the instrument inserted (see FIG. 1) is that for the side corresponding to the location of the fetal occiput. In FIG. 1 insertion of the blade is made at the left side of the maternal pelvis a the blade is termed a left hand blade. When insertion is made from the opposit side namely, from an approach at the right side of the maternal pelvis, the blade is considered a right hand blade. The blade is introduced as with other instruments, being lifted toward the side wall of the pelvis, remaining placed as through for a direct position. The blade being inserted, a uterine contraction is awaited. While this is taking place the scoop is applied in such a way by means of a moderate rotation of the handgrip, to make close contact with the fetal head. The tip of the scoop makes contact with the fetal head above the axis of rotation. The axis of rotation lies at the junction of the cervical column with the fetal occiput, which will vary in its placement according to the degree of flexion of the fetal head, which will change the magnitudes of the forces acting on the latter.

Figure 3:
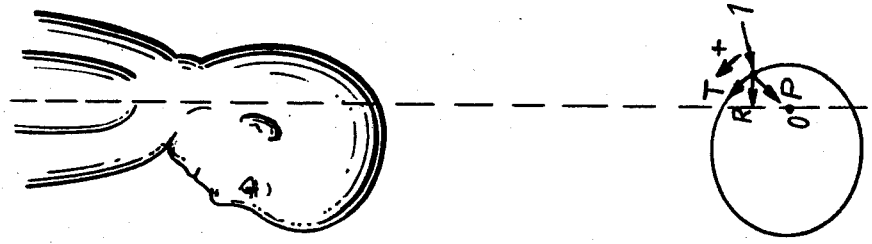
FIGS. 2 and 3 are schematic illustrations exemplifying a fetal head with different longitudinal axes of the head, showing the manner in which the invention can be practiced.

The position of the axis of rotation is important. In FIG. 3, a force P coincides with the axis of rotation "0" and does not therefore produce a couple, its value being equal to zero, only a tangential force T being in action.

Figure 2:
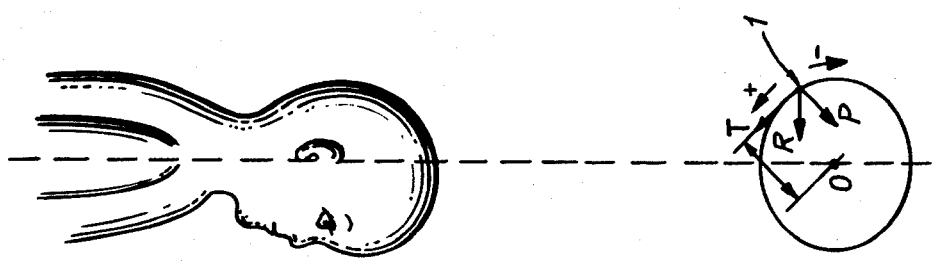

In FIG. 2, as the position of the axis of rotation "0" recedes from the point of application 1 of a force R, as occurs when the fetal head deflects, the force P is not equal to zero due to the creation of a moment (force X the distance perpendicular to the line of action). Force P opposes force T, impeding the desired rotation of the fetal head.

The novel method can be performed in two ways, according to whether the fetal head is seen or not during the uterine contraction. The rotation procedure must be effected when the fetal head is in sight.

First method (FIG. 1). This is employed when the fetal head 1 is not very visible during the uterine contraction. The scoop 12 is inserted in the same way as with other instruments. After it is in place, the handgrip 13 is held by the right hand as in left-hand applications and the perineum 4 is depressed by the left hand. For right-hand applications, the procedure is the same except for the hands being changed.

Figure 4:
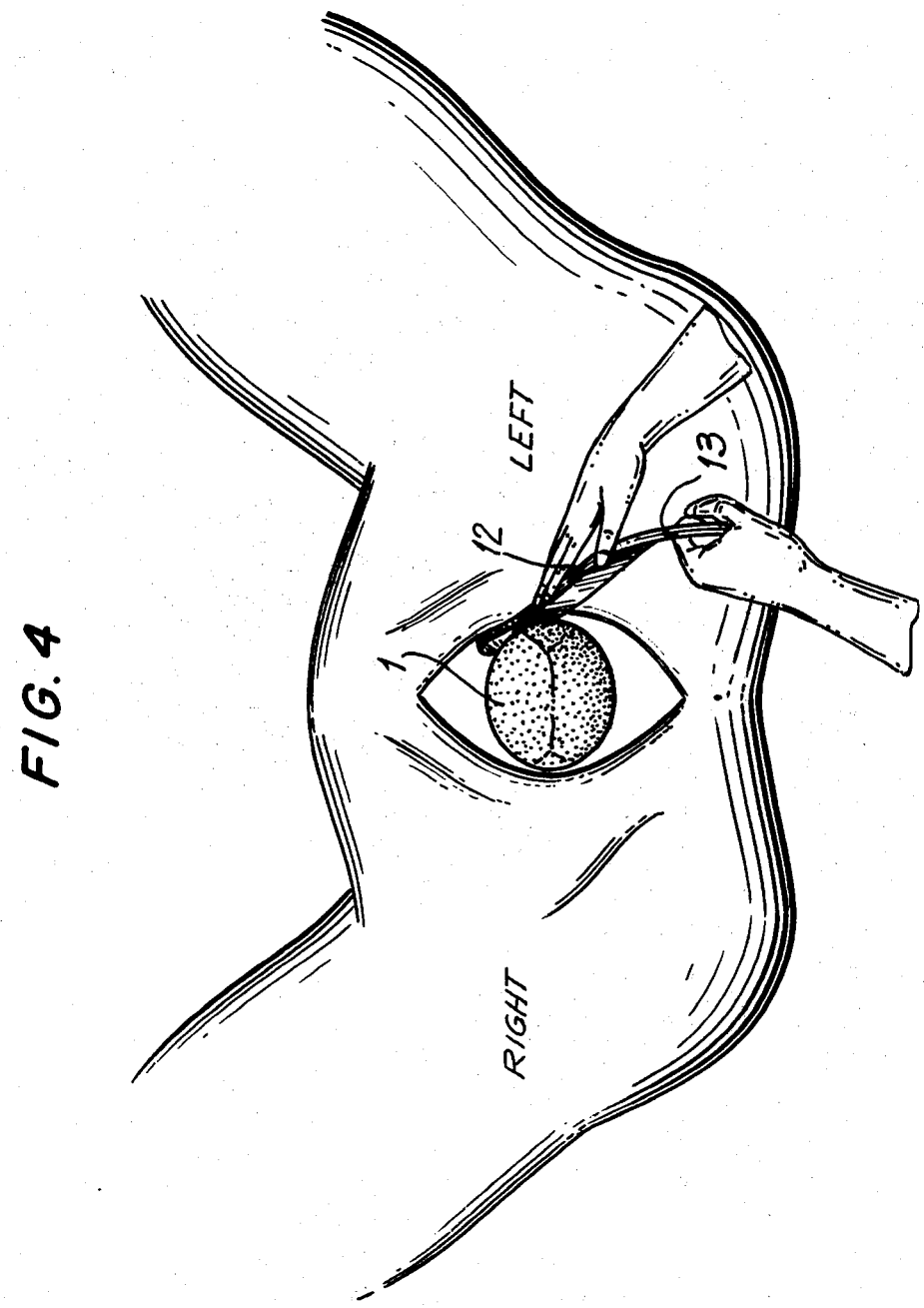
FIG. 4 is a schematic illustration similar to that of FIG. 1 but of an alternative manner of practicing the method.

Second method (FIG. 4). This is used when the fetal head 1 is seen although it may be seen only in part during the uterine contraction. The scoop 12 is introduced in the same way as with other instruments. After the blade is inserted, the handgrip 13 is grasped by the left hand as the left-hand position approaches, the right hand resting on the proximal portion of the scoop 12, so that the forces are exerted in the correct direction and no leverage is produced on the maternal tissues. The procedure is similar for right-hand approaches, the hands being changed. Once the rotation of the fetal head has been effected, the instrument can be withdrawn and the delivery can be spontaneously continued. On other occasions, fetal extraction can be assisted by the same blade or by applying both blades if that be necessary. The procedure is the same for all non-direct varieties of positions of the fetal head, whether right or left, for which reason we have only to bear in mind the application of the force relative to the axis of rotation. The inventive method and instrument achieve the rotation in all of the different positions of the fetal head, one of its greater advantages being therefore that training in its correct and rapid use is thus made easy.

The proposed instrument consists of two blades, right and left, independent and not interjointed. FIGS. 5 and 6 show plan and front elevational elevation views of the left blade. The blade is composed of a solid scoop, 12, the pedicle 15 and the handgrip 13 shaped like a pistol grip. The scoop exhibits a double pelvic curvature $R_1$ and $R_2$, one horizontal cephalic curvature $R_3$ and one vertical cephalic curvature $R_4$ whose radius is less than $R_3$. The above-mentioned radii are less than those of the scoops currently in use. The tip or nib of the scoop 12 has an angle alpha to the centerline of the instrument, similar to an angle beta made by the axis of the handgrip and the centerline of the instrument. FIG. 7 shows a section of the pedicle 15 in FIG. 6, and FIG. 8 shows the cross section of scoop 12 in FIG. 6.

We claim:

1. A process for rotation of the fetal head during childbirth, comprising the steps of: using a force through the agency of spatulas by applying the principle of wheel rotation for rotating the head in any of its presentations of position, to reduce fetal and maternal lesions, as well as the necessity of cesarean sections; rotating the head by applying the force at a point corresponding to the zone of the occipital bone; and utilizing as the axis of rotation, the rotation axis of the head passing through the junction of the cervical column with the fetal occiput.

2. The process as defined in claim 1, utilizing a spatula having a handgrip and scoop and pedicle portions and further comprising the step of inserting the spatula in the side of the maternal pelvis that corresponds to the fetal occiput.

3. The process as defined in claim 2, for situations where the head is not visible during the uterine contraction after the inserting step, further comprising the steps of holding the handgrip of the spatula in one hand with the scoop in lateral positional presentation with respect to the fetal head, and depressing the perineum by the other hand, in order to effect rotation with view of the fetal head.

4. The process as defined in claim 2, for situations where the fetal head is visible during the uterine contraction after the inserting step, further comprising the steps of taking the handgrip of the spatula in one hand with the scoop in lateral positional presentation with respect to the fetal head, and resting the other hand on the proximal portion of the scoop portion of the spatula and part of the pedicle portion thereof, in such a manner that on the occurrence of the uterine contraction there will be an area of close contact between the scoop portion and the fetal head.

* * * * *